(12) United States Patent
Diamond et al.

(10) Patent No.: US 7,235,625 B2
(45) Date of Patent: Jun. 26, 2007

(54) MULTIPLE AGENT THERAPY FOR SEXUAL DYSFUNCTION

(75) Inventors: Lisa E. Diamond, Princeton, NJ (US); Dennis C. Earle, Yardley, PA (US); Annette M. Shadiack, Somerset, NJ (US); Shubh D. Sharma, Cranbury, NJ (US); Carl Spana, West Harrison, NY (US)

(73) Assignee: Palatin Technologies, Inc., Cranbury, NJ (US)

( * ) Notice: Subject to any disclaimer, the term of this patent is extended or adjusted under 35 U.S.C. 154(b) by 0 days.

(21) Appl. No.: 11/139,730

(22) Filed: May 26, 2005

(65) Prior Publication Data

US 2005/0222014 A1    Oct. 6, 2005

Related U.S. Application Data

(60) Provisional application No. 60/575,082, filed on May 27, 2004.

(51) Int. Cl.
*A61K 38/00* (2006.01)
*A61K 38/12* (2006.01)

(52) U.S. Cl. .................. 530/312; 530/317; 530/321; 530/328; 530/329; 530/300; 514/9; 514/11; 514/12; 514/15; 514/16; 514/18; 424/9.1; 436/811

(58) Field of Classification Search ............ 530/312, 530/317, 321, 300, 328, 329; 514/9, 11, 514/12, 15, 16, 18; 424/9.1; 436/811
See application file for complete search history.

(56) References Cited

U.S. PATENT DOCUMENTS

| | | | |
|---|---|---|---|
| 5,576,290 | A | 11/1996 | Hadley |
| 5,674,839 | A | 10/1997 | Hruby et al. |
| 5,714,576 | A | 2/1998 | Hruby et al. |
| 6,051,555 | A | 4/2000 | Hadley |
| 6,350,430 | B1 | 2/2002 | Dooley et al. |
| 6,376,509 | B1 | 4/2002 | Bakshi et al. |
| 6,579,968 | B1 | 6/2003 | Blood et al. |
| 6,608,082 | B1 | 8/2003 | Basu et al. |
| 6,613,874 | B1 | 9/2003 | Mazur et al. |
| 6,794,489 | B2 | 9/2004 | Blood et al. |
| 2003/0069169 | A1 | 4/2003 | Macor et al. |
| 2004/0138136 | A1 | 7/2004 | Sharma et al. |
| 2004/0192676 | A1 | 9/2004 | Chen et al. |
| 2004/0208829 | A1 | 10/2004 | Rubsamen et al. |
| 2004/0266821 | A1 | 12/2004 | Ujjainwalla et al. |
| 2005/0075344 | A1 | 4/2005 | Backer et al. |

FOREIGN PATENT DOCUMENTS

| | | |
|---|---|---|
| EP | A-0463756 | 4/1995 |
| EP | A-0526004 | 10/1997 |
| EP | A-0995750 | 4/2000 |
| EP | A-0995751 | 6/2005 |
| WO | WO 93/06104 | 4/1993 |
| WO | WO 93/07124 | 4/1993 |
| WO | WO 93/07149 | 4/1993 |
| WO | WO 93/12095 | 6/1993 |
| WO | WO 94/05661 | 1/1994 |
| WO | WO 95/19978 | 7/1995 |
| WO | WO 96/26940 | 9/1996 |
| WO | WO 99/24433 | 5/1999 |
| WO | WO 99/54333 | 10/1999 |
| WO | WO 00/24745 | 5/2000 |
| WO | WO 00/53148 | 9/2000 |
| WO | WO 01/00224 | 1/2001 |
| WO | WO 01/13112 | 2/2001 |
| WO | WO 01/27112 | 4/2001 |
| WO | WO 01/27113 | 4/2001 |
| WO | WO 02/064091 | 8/2002 |
| WO | WO 02/069905 | 9/2002 |
| WO | WO 03/006620 | 1/2003 |
| WO | WO 2004/005324 | 1/2004 |
| WO | WO 2005/079574 | 9/2005 |

OTHER PUBLICATIONS

M. E. Hadley et al., Discovery and development of the novel melanogenic drugs, in *Integration of Pharmaceutical Discovery and Development: Case Studies*, edited by Borchardt et al., Plenum Press, New York (1998).
R. T. Dorr et al., Evaluation of Melanotan-II, A Superpotent Cyclic Melanotropic Peptide in a Pilot Phase-I Clinical Study. *Life Sci.* 58:1777-1784 (1996).
L. H. T. Van der Ploeg etr al., A Role for the Melanocortin 4 Receptor in Sexual Function. *P.N.A.S.*, 99:11381-11386 (2002).
H. Wessells et al., *J. Urology* 160:389-393 (1998).
H. Wessells et al., *Urology* 56:641-646 (2000).
H. Wessells et al., *Intl. J. Impotence Res.* 12:S74-S79 (2000).
R. Vernulapalli et al., Activation of Central Melanocortin Receptors by MT-11 Increases Cavernosal Pressure in Rabbits by the Neuronal Release of NO. *British Journal of Pharmacology*, 134:1705-1710 (2001).
A. Nehra et al., Rationale for Combination Therapy of Intraurethral Prostaglandin $E_1$ and Sildenafil in the Salvage of Erectile Dysfunction Patients Desiring Noninvasive Therapy. *Int'l Journal of Impotence Research*, 14(S1):S38-S42 (2002).

(Continued)

*Primary Examiner*—Chih-Min Kam
(74) *Attorney, Agent, or Firm*—Stephen A. Slusher

(57) ABSTRACT

Multiple agent therapy for treatment of sexual dysfunction, including male erectile dysfunction, with sequential administration a type V phosphodiesterase inhibitor (PDE-5), such as sildenafil, preferably wherein the PDE-5 inhibitor is administered by oral dose means, and a melanocortin 3 and/or 4 receptor agonist, such as Ac-Nle-cyclo(-Asp-His-D-Phe-Arg-Trp-Lys)-OH (PT-141) preferably wherein the PT-141 is formulated for and administered by intranasal means, and further preferably wherein the PDE-5 inhibitor is administered prior to PT-141.

22 Claims, 3 Drawing Sheets

OTHER PUBLICATIONS

F. Sommer and U. Engelmann, Future Options for Combination Therapy in the Management of Erectile Dysfunction in Older Men. *Drugs and Aging*, 9:555-564 (2004).

U. Gresser and C.H. Gleiter, Erectile Dysfunction: Comparison of Efficacy and Side Effects of the PDE-5 Inhibitors SIldenafil, Vardenafil and Tadalafil, Review of the Literature. *European J. of Med. Res.*, 7:435-446 (2002).

P.C. Souverein et al., Incidence and Determinants of Sildenafil (dis)continuation: the Dutch Cohort of Sildenafil Users. *Int. J. Impot. Res.* 14:259-265 (2002).

L.E. Diamond et al., Double-blind, Placebo-Controlled Evaluation of the Safety, Pharmacokinetic Properties and Pharmacodynamic effects of Intranasal PT-141, a Melanocortin Receptor Agonist, in Healthy Males and Patients with Mild-to-Moderate Erectile Dysfunction. *Int. J. Impot. Res.* 16:51-59 (2004).

*Synthetic Peptides: A User's Guide*, G. A. Grant, editor, W.H. Freeman & Co., New York, 1992, the teachings of which are incorporated herein by reference, including the text and table set forth at pp. 11 through 24.

V. J. Hruby, F. Al-Obeidi and W. Kazmierski: *Biochem. J.* 268:249-262, 1990.

C. Toniolo: *Int. J. Peptide Protein Res.* 35:287-300, 1990.

W. L. Furlow, Prevalence of Impotence in the United States. *Med. Aspects Hum. Sex.* 19:13-16 (1985.

F. E. Kaiser, Erectile Dysfunction in the Aging Man. *Med. Clin. N. Amer.* 83:1267-78 (1999).

Rotella D P, *J. Med Chem.* 43:1257 (2000).

M. E. Hadley et al., Discovery and development of the novel melanogenic drugs, in *Integration of Pharmaceutical Discovery and Development: Case Studies*, edited by Borchardt et al., Plenum Press, New York (1998), p. 575-595.

Rotella D P, *J. Med Chem.* 43:1257-1263 (2000).

MULTIPLE AGENT THERAPY FOR SEXUAL DYSFUNCTION

CROSS-REFERENCE TO RELATED APPLICATIONS

This application claims priority to and the benefit of the filing of U.S. Provisional Patent Application Ser. No. 60/575,082, entitled "Multiple Agent Therapy for Sexual Dysfunction", filed on May 27, 2004, and the specification and claims thereof are incorporated herein by reference.

BACKGROUND OF THE INVENTION

1. Field of the Invention (Technical Field)

The present invention relates to a method and multiple agents for treatment of sexual dysfunction, including male erectile dysfunction, including separate and preferably sequential administration of a melanocortin 3 and/or 4 receptor agonist, such as Ac-Nle-cyclo(-Asp-His-D-Phe-Arg-Trp-Lys)-OH (PT-141), preferably by one route of administration, such as intranasal (IN), and a type V phosphodiesterase (PDE-5) inhibitor, such as Viagra®, a trademark for a brand of sildenafil, preferably by another route of administration, such as oral.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

In the medical and pharmaceutical arts, any of a variety of drugs are known for treatment of sexual dysfunction such as male erectile dysfunction. One known class of drugs are PDE-5 inhibitors. PDE-5 inhibitors include Viagra®, a brand of sildenafil, Levitra®, a brand of monohydrochloride salt of vardenafil, and Cialis®, a brand of tadalafil, among pharmaceutical products approved by the U.S. Food and Drug Administration, as well as a number of other compounds. In general, PDE-5 inhibitors increase the persistence of cyclic guanosine monophosphate in the corpus cavernosum, thereby enhancing erectile response.

Another class of drugs are agonists of the melanocortin receptor, such as those disclosed in the following publications, which are incorporated here by reference in their entirety: M. E. Hadley et al., Discovery and development of the novel melanogenic drugs, in *Integration of Pharmaceutical Discovery and Development: Case Studies*, edited by Borchardt et al., Plenum Press, New York (1998); R. T. Dorr et al., Evaluation of Melanotan-II, A Superpotent Cyclic Melanotropic Peptide in a Pilot Phase-I Clinical Study. *Life Sci.* 58:1777–1784 (1996); L. H. T. Van der Ploeg etr al., A Role for the Melanocortin 4 Receptor in Sexual Function. *P.N.A.S.*, 99:11381–11386 (2002). The agonists can be melanocortin stimulation hormone (MSH), including $\alpha$-, $\beta$-, and $\gamma$-MSH, or adrenocorticotropin (ACTH). Melanocortin receptor-specific compounds have been explored for use of treatment of sexual dysfunction. In one report, a cyclic $\alpha$-melanocyte-stimulating hormone ("$\alpha$-MSH") analog, called Melanotan-II or MT-II, was evaluated for erectogenic properties for treatment of men with psychogenic and organic erectile dysfunction. H. Wessells et al., *J. Urology* 160:389–393 (1998), H. Wessells et al., *Urology* 56:641–646 (2000), and H. Wessells et al., *Intl. J. Impotence Res.* 12:S74–S79 (2000); see also U.S. Pat. No. 5,576,290, issued Nov. 19, 1996 to M. E. Hadley, entitled *Compositions and Methods for the Diagnosis and Treatment of Psychogenic Erectile Dysfunction* and U.S. Pat. No. 6,051,555, issued Apr. 18, 2000, also to M. E. Hadley, entitled *Stimulating Sexual Response in Females*. The peptides used in U.S. Pat. Nos. 5,576,290 and 6,051,555 are also described in U.S. Pat. No. 5,674,839, issued Oct. 7, 1997, to V. J. Hruby, M. E. Hadley and F. Al-Obeidi, entitled *Cyclic Analogs of Alpha-MSH Fragments*, and in U.S. Pat. No. 5,714,576, issued Feb. 3, 1998, to V. J. Hruby, M. E. Hadley and F. Al-Obeidi, entitled *Linear Analogs of Alpha-MSH Fragments*. Additional related peptides are disclosed in U.S. Pat. Nos. 5,576,290, 5,674,839, 5,714,576 and 6,051,555. Other peptides are described in a number of publications, including U.S. Pat. Nos. 6,350,430, 6,608,082 and 6,613,874. These peptides are described as being useful for both the diagnosis and treatment of psychogenic and organic sexual dysfunction in males and females. These peptides are related to the structure of melanocortin specific peptides.

A preferred melanocortin receptor agonist is Ac-Nle-cyclo(-Asp-His-D-Phe-Arg-Trp-Lys)-OH, called PT-141, as disclosed in U.S. Pat. Nos. 6,579,968 and 6,794,489, incorporated herein by reference. It is believed that melanocortin agonists, including PT-141, amplify the release of nitric oxide from nitrergic nerve fibers, and the cavernosal nerve in particular, enhancing erectile response by enhancing normal central and peripheral reflex pathways. R. Vemulapalli et al., Activation of Central Melanocortin Receptors by MT-II Increases Cavernosal Pressure in Rabbits by the Neuronal Release of NO. *British Journal of Pharmacology*, 134:1705–1710 (2001). Other preferred melanocortin receptor agonists are disclosed in U.S. patent application Ser. No. 10/638,071, published as U.S. Patent Application Publication No. 20040138136 A1, entitled "Cyclic Peptide Compositions and Methods for Treatment of Sexual Dysfunction," incorporated herein by reference.

Combination therapy, particularly with PDE-5 inhibitors such as sildenafil, has been considered for a number of years. For example, one article proposes combination therapy of intraurethral prostaglandin $E_1$ and sildenatil (A. Nehra et al., Rationale for Combination Therapy of Intraurethral Prostaglandin $E_1$ and Sildenafil in the Salvage of Erectile Dysfunction Patients Desiring Noninvasive Therapy. *Int'l Journal of Impotence Research*, 14(S1):S38–S42 (2002)), another article describes potential combinations with $\alpha$-andrenoceptor antagonists or testosterone replacement therapy (F. Sommer and U. Engelmann, Future Options for Combination Therapy in the Management of Erectile Dysfunction in Older Men. *Drugs and Aging*, 9:555–564 (2004). WO 00/53148 (Merck) discloses and claims a "method for the treatment of erectile dysfunction which comprises administering to a human subject in need of such treatment an effective amount of an agonist of the melanocortin receptor in combination with an effective amount of a cyclic-GMP-specific phosphodiesterase inhibitor or an alpha-andrenergic receptor antagonist." MT-II is a disclosed melanocortin receptor agonist and sildenafil is a disclosed PDE-5 inhibitor. The entire application is prophetic; that is, there is no actual data reported or disclosed. Hypothetical formulations disclosed include, for example, 5 mg of a melanocortin agonist and 10 mg of a PDE-5 inhibitor combined together in a capsule. The Merck application does not disclose intranasal administration of MT-II. Additionally, the Merck application does not disclose that a peptide-based melanocortin agonist may be administered by an intranasal route and a PDE-5 inhibitor administered by an oral route, or that the agents may be sequentially administered at timed intervals to obtain optimal results. Nor does the application disclose a synergistic effect, such as by administering a sub-therapeutic dose of each agent, which nonetheless results in a desired therapeutic result.

WO 02/069905 and United States Patent Application US 2003/0069169 disclose a "method of regulating . . . cAMP production in a mammal comprising administering . . . a combination of (i) an amount of at least one compound effective for agonizing a melanocortin-receptor selected from MC-1R and MC-4R, and (ii) an amount of at least one compound effective for inhibiting cAMP phosphodiesterase." Specific disclosures are only to PDE-3, -4, -7 or -8 inhibitors, and a number of specific diseases are disclosed (e.g., inflammatory bowel disease, rheumatoid arthritis, asthma, etc.), but not sexual dysfunction. Again, there is only disclosure of "combination" drug, that is, a single pharmaceutical preparation including both a melanocortin receptor agonist and a PDE inhibitor.

A number of other patents and patent applications contain prophetic disclosures of combination therapy where one agent is a melanocortin receptor agonist and a second agent is a PDE-5 inhibitor; representative examples include U.S. Pat. No. 6,894,040 (disclosing administering a xanthine phosphodiesterase V inhibitor as "combination therapy" with any of a long list of agents including a melanocortin receptor agonist); U.S. Pat. No. 6,376,509 (disclosing a small molecule asserted to be a melanocortin receptor agonist in a pharmaceutical composition including a PDE-5 inhibitor); U.S. Published Patent Application 2004/0192676 (disclosing a small molecule asserted to be a melanocortin receptor agonist in a pharmaceutical composition including sildenafil); U.S. Published Patent Application 2004/0266821 (disclosing an acylated piperidine derivative asserted to be a melanocortin receptor agonist in combination with a PDE-5 inhibitor such as sildenafil); and U.S. Published Patent Application 2005/0075344 (disclosing a small molecule asserted to be a melanocortin receptor agonist in combination with a PDE-5 inhibitor such as sildenafil). U.S. Published Patent Application 2004/0208829 discloses an aerosol formulation to be inhaled into a patient's lungs; in one embodiment there is disclosed an aerosol formulation including an active ingredient selected from one or more of a lengthy list of agents, which agents include PDE-5 inhibitors and a melanocortin receptor agonist. Each of the foregoing are, with respect to any combination therapy or formulation, merely prophetic, and do not include any clinical or animal study data.

It is well recognized that PDE-5 inhibitors, such as sildenafil, vardenafil or tadalafil, can have adverse side effects, such as headache, facial flushing, nasal congestion, changes in vision and the like. U. Gresser and C. H. Gleiter, Erectile Dysfunction: Comparison of Efficacy and Side Effects of the PDE-5 Inhibitors Sildenafil, Vardenafil and Tadalafil, Review of the Literature. *European J. of Med. Res.*, 7:435–446 (2002). Side effects and other adverse events are generally dose dependent, with increasing frequency and severity at higher doses. This results in discontinuation of use of PDE-5 inhibitors by patients over time. P. C. Souverein et al., Incidence and Determinants of Sildenafil (dis)continuation: the Dutch Cohort of Sildenafil Users. *Int. J. Impot. Res.* 14:259–265 (2002). Similar dose dependent side effects and adverse events results from IN PT-141 administration. L. E. Diamond et al., Double-blind, Placebo-Controlled Evaluation of the Safety, Pharmacokinetic Properties and Pharmacodynamic effects of Intranasal PT-141, a Melanocortin Receptor Agonist, in Healthy Males and Patients with Mild-to-Moderate Erectile Dysfunction. *Int. J. Impot. Res.* 16:51–59 (2004). Thus there is need for a therapeutic method for treatment of erectile dysfunction in males, and sexual dysfunction generally, which results in desired efficacy, without limiting side effects and other adverse events. It is against this background that the invention was made.

BRIEF SUMMARY OF THE INVENTION

The invention includes a method of treating sexual dysfunction in a patient, including the steps of oral administration of a type V phosphodiesterase (PDE-5) inhibitor and non-oral administration of a melanocortin receptor agonist, preferably a melanocortin 3 and/or melanocortin 4 receptor agonist. A preferred melanocortin receptor agonist is PT-141, and a preferred non-oral administration thereof is by intranasal (IN) administration. In this method the PDE-5 inhibitor may be sildenafil, vardenafil or tadalafil. The quantity of PDE-5 inhibitor administered may not be sufficient, if administered as monotherapy, to independently initiate the desired pharmacological response in the patient. Similarly the quantity of PT-141 administered may not be sufficient, if administered as monotherapy, to independently initiate the desired pharmacological response in the patient. It is possible that neither the quantity of PDE-5 inhibitor nor the quantity of PT-141 administered is independently sufficient, if either is administered as monotherapy, to initiate the desired pharmacological response in the patient. However, in this method the quantity of PDE-5 inhibitor administered in conjunction with the quantity of PT-141 administered is sufficient, as multiple agent therapy, to initiate the desired pharmacological response in the patient.

In this method the patient may be a male patient, the sexual dysfunction may be erectile dysfunction, and the desired pharmacological response is the ability to attain or sustain an erection of sufficient rigidity for sexual intercourse.

In this method sildenafil may be administered in any quantity between about 25 mg and 50 mg, and up to about 75 mg to about 100 mg, and preferably the quantity is about 25 mg. PT-141 may be administered in any quantity between about 2.5 mg and about 12.5 to about 15 mg, and preferably the quantity is about 7.5 mg. The PDE-5 inhibitor is preferably administered prior to the administration of PT-141. In one embodiment the PDE-5 inhibitor is administered between 5 and 45 minutes prior to the administration of PT-141, preferably between about 10 and 30 minutes prior to the administration of PT-141. In another embodiment PT-141 is administered about 30 minutes prior to the attainment of the average peak plasma concentration, or $T_{max}$, of the PDE-5 inhibitor. In yet another embodiment, PT-141 is administered no later than about 30 minutes prior to the end of the average half-life of the PDE-5 inhibitor. It is also possible and included within the invention that the PDE-5 inhibitor is administered to maintain a steady-state plasma concentration and PT-141 is administered at anytime thereafter.

In this method the patient may not be therapeutically responsive to a single dose of either the PDE-5 inhibitor or PT-141 administered as monotherapy. Fewer side effects, or less severe side effects, or both, result from use of the described method than would result from administration of a therapeutically effective amount of a single agent sufficient to initiate the desired pharmacological response in the patient. In this method, the patient-reported quality of erection score in one embodiment is superior to that obtained from administration of a therapeutically effective amount of a single agent, including a single agent sufficient to initiate the desired pharmacological response in the patient.

According to one embodiment of the present invention, peptide Ac-Nle-cyclo(-Asp-His-D-Phe-Arg-Trp-Lys)-OH is used for the manufacture of a medicament for the treatment by nasal administration of sexual dysfunction. The peptide is used in conjunction with a PDE-5 inhibitor. In one embodiment, the PDE-5 inhibitor is, for example, sildenafil, vardenafil, tadalafil or a combination thereof. In another embodiment, the PDE-5 inhibitor is for use by oral administration. The multi-agent therapy is useful for treating sexual dysfunction for example male erectile dysfunction.

According to still another embodiment of the present invention, the peptide Ac-Nle-cyclo(-Asp-His-D-Phe-Arg-Trp-Lys)-OH is used for the manufacture of a medicament for treatment by multiple agent therapy with a PDE-5 inhibitor for sexual dysfunction, wherein the amount of each of the peptide Ac-Nle-cyclo(-Asp-His-D-Phe-Arg-Trp-Lys)-OH and the PDE-5 inhibitor is not sufficient, if administered as monotherapy, to independently initiate the desired pharmacological response in the patient. In one embodiment of the present invention, the peptide Ac-Nle-cyclo(-Asp-His-D-Phe-Arg-Trp-Lys)-OH is employed for manufacture of a medicament for treatment by nasal administration, the PDE-5 inhibitor is employed for manufacture of a medicament for treatment by oral administration, and the desired pharmacological response is the ability to attain or sustain an erection of sufficient rigidity for sexual intercourse. The PDE-5 inhibitor is for example, sildenafil, vardenafil, tadalafil or a combination thereof.

According to yet another embodiment of the present invention, the peptide Ac-Nle-cyclo(-Asp-His-D-Phe-Arg-Trp-Lys)-OH is used in the manufacture of a medicament for intranasal administration for use in the treatment of erectile dysfunction in a male, wherein the peptide Ac-Nle-cyclo(-Asp-His-D-Phe-Arg-Trp-Lys)-OH increases cGMP levels to an amount sufficient to produce an erection sufficient for sexual intercourse when the peptide Ac-Nle-cyclo(-Asp-His-D-Phe-Arg-Trp-Lys)-OH is administered at a sub-therapeutic dose and administered subsequent to a sub-therapeutic dose of a PDE-5 inhibitor.

One aspect of the present invention is to provide a method for multiple agent therapy for sexual dysfunction, including male erectile dysfunction, wherein pharmacologically active drugs are sequentially administered.

Another aspect of the invention is to provide a method for treating sexual dysfunction while minimizing side effects by administering multiple agents where each agent, if given independently, which is to say as a monotherapy agent, is a sub-therapeutic dose, but when each agent is given sequentially, which is to say as a component of multiple agent therapy, the synergistic effect thereof is therapeutic.

Another aspect of the invention is to provide a method for administering two agents, such as administering two agents sequentially, for treatment of sexual dysfunction, wherein each agent is administered by a different route.

Another aspect of the invention is to provide a method for administering two agents, such as administering two agents sequentially, for treatment of sexual dysfunction, wherein each agent is administered by a different route, utilizing a peptide-based melanocortin receptor agonist administered by a non-oral route, such as nasal delivery, and a PDE-5 inhibitor that is a small molecule administered by an oral route.

Yet another aspect is to provide a method for timed administration of sequentially administered agents, such that an optimal therapeutic effect results.

Yet another aspect of the invention is to provide a method for treating patients not responsive to a PDE-5 inhibitor alone, the method including administering both PT-141 and a PDE-5 inhibitor, wherein the PDE-5 inhibitor is administered prior to administration of PT-141.

Yet another aspect of the invention is to provide a method for treating patients not responsive to a PDE-5 inhibitor alone, the method including administering both PT-141 and a PDE-5 inhibitor, wherein the PDE-5 inhibitor is administered at approximately the same time as administration of PT-141.

Yet another aspect of the invention is to provide a method for treating patients not responsive to a PDE-5 inhibitor alone, the method including administering both PT-141 and a PDE-5 inhibitor, wherein the PDE-5 inhibitor is administered subsequent to administration of PT-141.

Yet another aspect of the invention is to provide a method for treating patients not responsive to a maximum recommended dose of a PDE-5 inhibitor, the method including administering both PT-141 and a PDE-5 inhibitor, wherein the PDE-5 inhibitor is administered prior to, at approximately the same time as, or subsequent to administration of PT-141, and further wherein the dose PT-141 is between about 2.5 mg and about 15 mg.

Yet another aspect of the invention is to provide a method for increasing the reliability of therapy for sexual dysfunction, such as with patients that are responsive to a PDE-5 inhibitor less than 100% of the time, such as less than about 50% of the time, by multiple agent therapy with a PDE-5 inhibitor and a melanocortin receptor agonist such as PT-141.

Yet another aspect of the invention is to provide a method for increased temporal duration of the therapeutic response in treatment of sexual dysfunction by oral administration of a PDE-5 inhibitor and non-oral administration, preferably IN administration, of a melanocortin receptor agonist, preferably PT-141.

Still another aspect of the present invention provides a method for treating sexual dysfunction by means of sequential administration of two agents in patients for whom a single agent is not efficacious.

Another aspect of the invention is that sequential administration of low doses of a PDE-5 inhibitor and PT-141 for treatment of sexual dysfunction provides a therapeutic effect equal or superior to administration of a high dose of any one single agent without the side effects attendant to administration of a high dose of any one single agent.

Other aspects and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The aspects of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention.

The drawings are only for the purpose of illustrating one or more preferred embodiments of the invention and are not to be construed as limiting the invention. In the drawings.

DETAILED DESCRIPTION OF THE INVENTION

Figure 1:
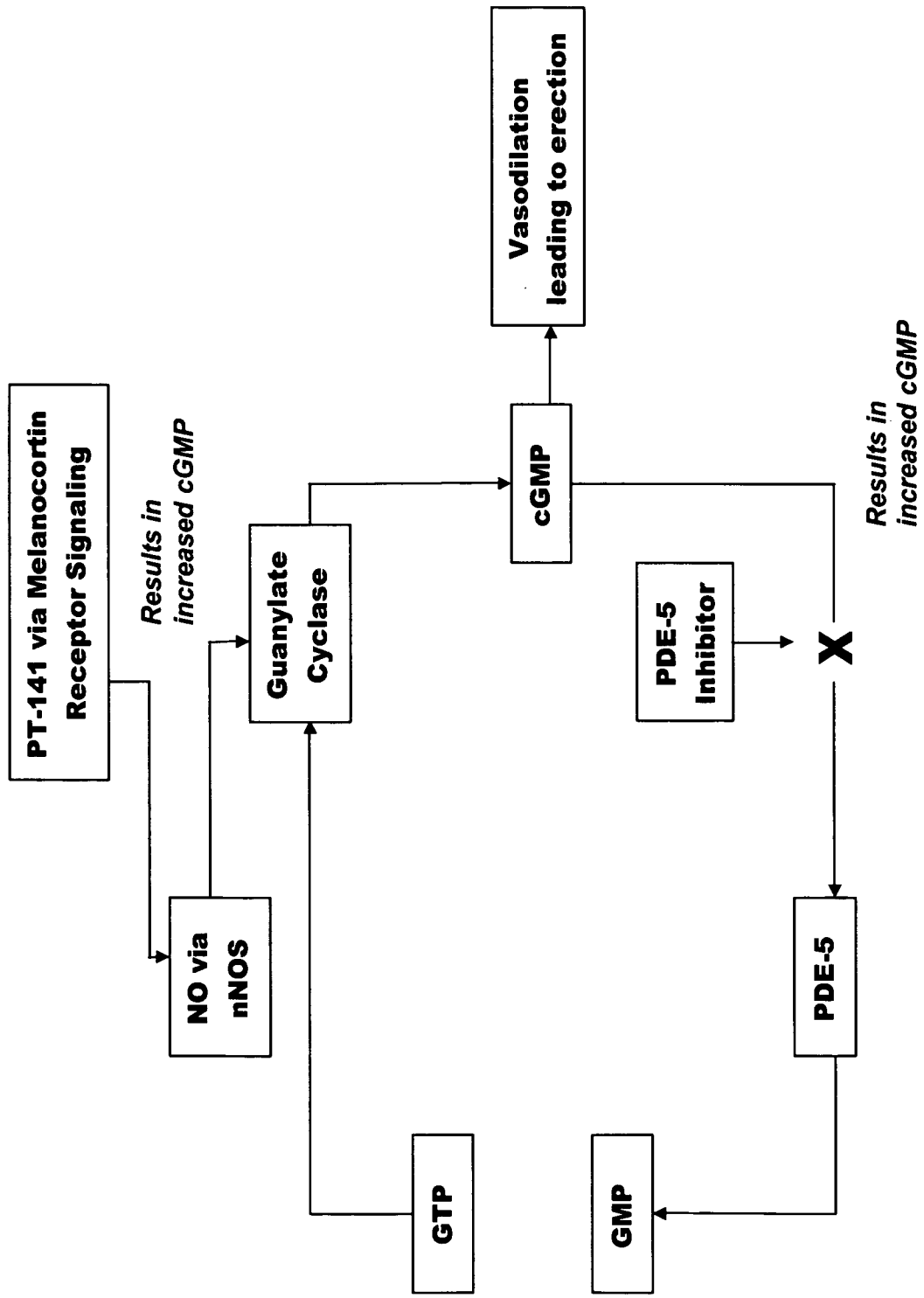
FIG. 1 is a diagram illustrating the presumptive pharmacological effects of administration of a PDE-5 inhibitor and PT-141 according to one embodiment of the invention.

Definitions. Before proceeding with the description of the invention, certain terms are defined as set forth herein.

The "amino acid" and "amino acids" used in this invention, and the terms as used in the specification and claims, include the known naturally occurring protein amino acids, which are referred to by both their common three letter abbreviation and single letter abbreviation. See generally *Synthetic Peptides: A User's Guide*, G. A. Grant, editor, W.H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; V. J. Hruby, F. Al-Obeidi and W. Kazmierski: *Biochem. J.* 268:249–262, 1990; and C. Toniolo: *Int. J. Peptide Protein Res.* 35:287–300, 1990; the teachings of all of which are incorporated herein by reference.

In the listing of compounds according to the present invention, the amino acid residues have their conventional meaning as given in Chapter 2400 of the *Manual of Patent Examining Procedure*, 8$^{th}$ Ed. Thus, "Nle" is norleucine; "Asp" is aspartic acid; "His" is histidine; "D-Phe" is D-phenylalanine; "Arg" is arginine; "Trp" is tryptophan; "Lys" is lysine; "Gly" is glycine; "Pro" is proline; "Tyr" is tyrosine, and "Ser" is serine. "Ac" refers to a peptide or amino acid sequence that is acetylated.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions utilized in the present invention encompass any composition made by admixing an active ingredient and one or more pharmaceutically acceptable carriers.

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and includes the inability to attain or sustain an erection of sufficient rigidity for coitus. Symptoms of erectile dysfunction include an inability to achieve or maintain an erection. An increase in erectile dysfunction is often associated with age or may be caused by a physical disease or as a side-effect of drug treatment. Erectile dysfunction (ED) may be due to psychogenic, vasculogenic and/or neurogenic disorders. This disorder affects 10 to 30 million men in the US and more than 140 million men worldwide. (W. L. Furlow, Prevalence of Impotence in the United States. *Med. Aspects Hum. Sex.* 19:13–16 (1985); F. E. Kaiser, Erectile Dysfunction in the Aging Man. *Med. Clin. N. Amer.* 83:1267–78 (1999)). Erectile dysfunction is confirmed following a clinical diagnosis of at least 6 months duration. Erectile dysfunction is conventionally defined as the inability to achieve or maintain an erection of the penis sufficient to permit satisfactory sexual intercourse, a definition developed by a National Institutes of Health Consensus Development Conference (NIH Consensus on Impotence. *J.A.M.A.* 270:83–90 (1993)). Erectile dysfunction of psychological origin (PED), in the absence of any organic cause, is the inability to initiate or maintain an erection due to depression, anxiety, stress, tension, guilt, relationship problems and/or the fear of failure to perform sexually. Unlike subjects with organic ED (OED), men with PED continue to have sleep-associated erections and may be able to achieve erections with masturbation. Psychological factors are the major cause of ED in about 20% of subjects presenting with symptoms of at least 6 months duration. OED is not a normal consequence of aging. Rather, it is the result of the diseases that occur with aging (such as atherosclerosis, diabetes mellitus and hypertension) and the associated medications used to treat them. The most common etiology of OED is vascular disease. Risk factors for vascular disease include cigarette smoking, hypertension, diabetes mellitus and hyperlipidemia. Vascular (arterial) disease results in ED through two mechanisms. Arterial occlusion prevents vasodilation and therefore the increase in blood flow needed for erection. Also, the ischemia from decreased blood flow to the corpus cavernosum may result in penile fibrosis and a decreased ability to trap blood within the penis, i.e., venous leakage. Thus, subjects with vascular disease may have decreased ability to achieve and maintain an erection. The second most common etiology of OED is autonomic dysfunction. This is due to diseases such as diabetes mellitus, stroke and Parkinson's disease. The autonomic dysfunction seen in these diseases impairs the parasympathetic innervation of the penis while sparing the sympathetic innervation, thereby preventing the vasodilation necessary for erection. The physiology of penile erection involves interaction of the vascular, neurological and hormonal systems of the body. Erection is produced by vasodilation of two arteries entering the paired corpora cavernosa (parallel vascularized cylinders extending from the ischial tuberosity to the glans). Erectile function is a coordinated interaction of the nervous system, blood supply and hormonal activity. An increase of arterial inflow of blood to the penis and a concomitant decrease of venous outflow produces the erection. A network of tiny distensible veins, known as sinusoids, swells from the temporary increase in blood flow and causes the penis to enlarge and stiffen. The expanded sinusoids compress veins that normally drain blood from the organ, and thus, trap blood within the sinusoidal network. The restricted blood outflow leads to an increase in intracavernosal pressure to a value that approximates the mean systemic arterial blood pressure. Impairment of the mechanisms that relax corporal smooth muscle, penile arteries, or sinusoids may result in varying degrees of erectile dysfunction.

"Female sexual dysfunction" is a disorder including female sexual arousal disorder. The term "sexual arousal disorder" includes a persistent or recurrent failure to attain or maintain the lubrication-swelling response of sexual excitement until completion of sexual activity. The *Draft Guidance for Industry, Female Sexual Dysfunction: Clinical Development of Drug Products for Treatment*, U.S. Food and Drug Administration, May 2000, lists four recognized components of female sexual dysfunction: decreased sexual desire; decreased sexual arousal; dyspareunia; and persistent difficulty in achieving or inability to achieve orgasm, with the components associated with personal distress, as determined by the affected woman. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be related to boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

By a melanocortin receptor "agonist" is meant an endogenous or drug substance or compound, including a compound such as PT-141, which can interact with a melanocortin receptor and initiate a pharmacological response, including but not limited to adenyl cyclase expression, characteristic of the melanocortin receptor.

Clinical Applications.

The compounds and methods disclosed herein can be used for both medical applications and animal husbandry or veterinary applications. Typically, the methods are used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

Melanocortin Receptor Agonists.

One embodiment of the present invention includes the use of deamidated α-MSH peptides, which are peptides that include the core α-MSH sequence His-Phe-Arg-Trp (SEQ ID NO:1), His-D-Phe-Arg-Trp, or homologs or analogs of either of the foregoing, in which the peptide is deamidated, which is to say that it does not include an —$NH_2$ group at the carboxyl terminus. In another embodiment of the present invention, the deamidated α-MSH peptide used in this invention has an —OH group at the carboxyl terminus, and is thus a free acid form of peptide.

In yet another embodiment of the present invention, the melanocortin receptor agonist is:

Ac-Nle-cyclo(-Asp-His-D-Phe-Arg-Trp-Lys)-OH        PT-141

The peptide of PT-141 has a formula of $C_{50}H_{68}N_{14}O_{10}$, and a net molecular weight of 1025.18. This peptide may be synthesized by conventional means, including either solid-phase or liquid-phase techniques, and purified to greater than 99% purity by HPLC, yielding a white powder that is a clear, colorless solution in water. The structure of PT-141 is:

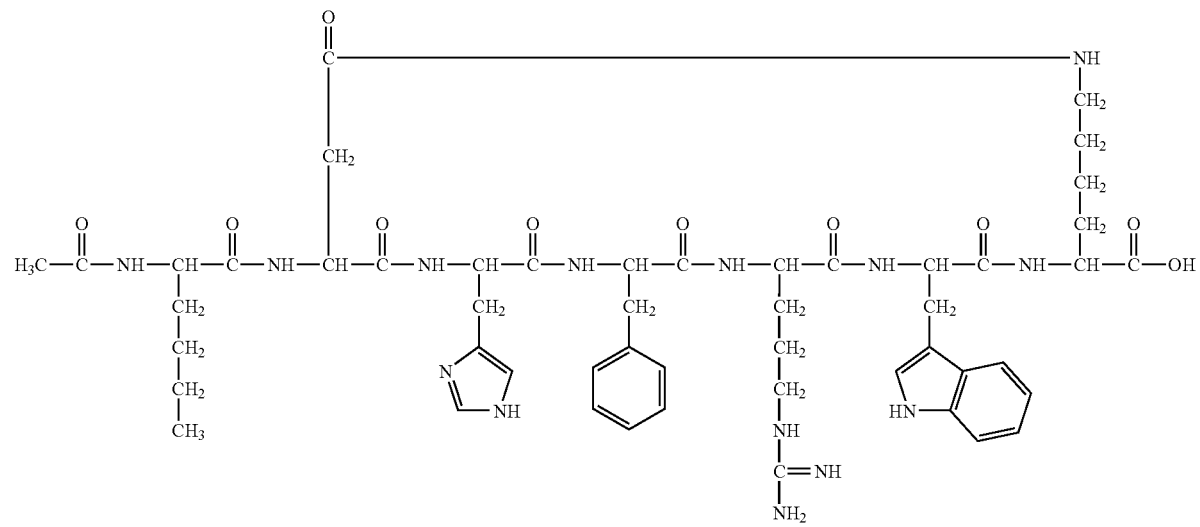

In one embodiment of the invention, PT-141 is synthesized by solid-phase synthesis and purified according to methods known in the art. Any of a number of well-known procedures utilizing a variety of resins and reagents may be used to prepare PT-141.

PT-141 may be in the form of any pharmaceutically acceptable salt. Acid addition salts of the compounds of this invention are prepared in a suitable solvent from the peptide and an excess of an acid, such as hydrochloric, hydrobromic, sulfuric, phosphoric, acetic, trifluoroacetic, maleic, citric, tartaric, oxalic, succinic or methanesulfonic acid. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

In a preferred embodiment, PT-141 is an acetate salt form, and is formulated in a buffered aqueous solution including glycerin, prepackaged in a metered unit dose intranasal delivery device. In alternative embodiments, PT-141 is any pharmaceutically acceptable salt form, and is formulated in any pharmaceutically acceptable aqueous solution, the aqueous solution optionally including one or more salts, such as sodium chloride, one or more acids, such as citric acid, and one or more additional ingredients, including cellulose or derivatives thereof, saccharides or polysaccharides such as dextrose, and any of a wide variety of surfactants, chelating agents and preservatives. In one preferred embodiment, PT-141 is administered to patients in volumes of 100 μL, with the quantity of PT-141 delivered determined by the concentration thereof. As described hereafter, in one preferred embodiment a metered unit dose contains 7.5 mg of PT-141.

While certain embodiments of the present invention are described primarily in the context of PT-141, it is to be understood that other melanocortin receptor agonists may be employed. For example, the metallopeptide melanocortin receptor agonists disclosed in WO 02/064091, filed on Feb. 13, 2001, and U.S. Ser. No. 10/640,755, filed on Aug. 13, 2003, both entitled *Melanocortin Metallopeptides for Treatment of Sexual Dysfunction*; and WO 01/13112, filed on Jun. 14, 2000, entitled *Melanocortin Metallopeptide Constructs, Combinatorial Libraries and Applications*, may be employed. In addition, the peptidomimetic melanocortin receptor agonists disclosed in U.S. Ser. No. 10/776,419, filed on Feb. 10, 2004, entitled *Peptidomimetics of Biologically Active Metallopeptides*; the pyrrolidine melanocortin receptor agonists disclosed in U.S. Ser. No. 10/766,657, filed on Feb. 10, 2004, entitled *Pyrrolidine Melanocortin-Specific Compounds*; and the bicyclic melanocortin receptor agonists disclosed in PCT/US04/01505, filed on Jan. 20, 2004, entitled *Bicyclic Melanocortin-Specific Compounds*, may also be employed. Also particular preferred are the piperazine melanocortin agonists disclosed in PCT/US04/01462, filed on Jan. 20, 2004 and U.S. Ser. No. 10/762,079, filed on Jan. 20, 2004, both entitled *Piperazine Melanocortin-Specific Compounds*; the melanocortin agonists disclosed in WO 03/006620, filed on Jul. 11, 2002, entitled *Linear and Cyclic Melanocortin Receptor-Specific Peptides*; WO 04/005324, filed on Jul. 9, 2003, entitled *Peptide Compositions for Treatment of Sexual Dysfunction*; PCT/US00/18217, filed on Jun. 29, 2000 and U.S. Ser. No. 10/040,547, filed on Jan. 4, 2002, entitled *Compositions and Methods for Treatment of Sexual Dysfunction*; and U.S. Ser. No. 10/638,071, filed on Aug. 8, 2003, entitled *Cyclic Peptide Compositions and Methods for Treatment of Sexual Dysfunction*. The entire disclosure of each of the foregoing are incorporated here by reference. It is to be understood that the foregoing listing of patent applications disclosing melanocortin receptor agonists is intended to only be exemplary, and that other melanocortin receptor agonists, whether heretofore known or hereafter developed, may similarly be used in the practice of this invention.

PDE-5 Inhibitors.

According to another embodiment of the present invention, PDE-5 inhibitors include:

5-[2-ethoxy-5-(4-methyl-1-piperazinylsulphonyl)phenyl]-1-methyl-3-n-propyl-1,6-dihydro-7H-pyrazolo[4,3-d]pyrimidin-7-one (sildenafil), also known as 1-[[3-(6,7-dihydro-1-methyl-7-oxo-3-propyl-1R-pyrazolo[4,3-d]pyrimidin-5-yl)-4-ethoxyphenyl]sulphonyl]-4-methylpiperazine (see EP-A-0463756 and U.S. Published Application No. 2003/0083228);

(6R, 12aR)-2,3,6,7,12,12a-hexahydro-2-methyl-6-(3,4-methylenedioxyphenyl)-pyrazino[2',1':6,1]pyrido[3,4-b]indole-1,4-dione (IC-351) (tadalafil), such as the compound of examples 1, 3, 7, 8, 78 and 95 of published international application WO 95/19978;

[2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, such as the compound of examples 20, 19, 337 and 336 of published international application WO 99/24433;

5-(2-ethoxy-5-morpholinoacetylphenyl)-1-methyl-3-n-propyl-1,6-dihydro-7H-pyrazolo[4,3-d]pyrimidin-7-one (see EP-A-0526004);

3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one (see WO 98/49166);

3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO 99/54333);

(+)-3-ethyl-5-[5-(4-ethylpiperazin-1-ylsulphonyl)-2-(2-methoxy-1-(R-)-methylethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-(-[(1R)-2-methoxy-1-methylethyl]oxy)pyridin-3-yl}-2-methyl-2,6-dihydro-7H-pyrazolo[4,3-d]pyrimidin-7-one (see WO 99/54333);

5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}4-ethylpiperazine (see WO 01/27113, Example 8);

5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see WO 01/27113, Example 15);

5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO 01/27113, Example 66);

5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see WO 01/27112, Example 124);

5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112, Example 132);

the compound of example 11 of published international application WO 93/07124 (EISAI);

compounds 3 and 14 from Rotella D P, *J. Med. Chem.* 43:1257 (2000);

4-bromo-5-(pyridylmethylamino)-6-[3-(4-chlorophenyl)-propoxy]-3(2H)-pyridazinone;

1-[4-[(1,3-benzodioxol-5-yl methyl)ainiono]-6-chloro-2-quinozolinyl]-4-piperidine-carboxylic acid, monosodium salt;

(+)-cis-5,6a,7,9,9,9a-hexahydro-2-[4-(trifluoromethyl)-phenylmethyl-5-methyl -cyclopent-4,5]imidazo[2,1-b]purin-4(3H)one;

furaziocillin;

cis-2-hexyl-5-methyl-3,4,5,6a,7,8,9,9a-octahydrocyclopent[4,5]-imidazo[2,1-b]purin-4-one; 3-acetyl-1-(2-chlorobenzyl)-2-propyl indole-6-carbox-ylate; 3-acetyl-1-(2-chlorobenzyl)-2-propylindole-6-carboxylate;

4-bromo-5-(3-pyridylmethylamino)-6-(3-(4-chlorophenyl)propoxy)-3-(2-H)pyridazinone;

1-methyl-5(5-morpholinoacetyl-2-n-propoxyphenyl)-3-n-propyl-1,6-dihydro-7H-pyrazolo(4,3-d)pyrimidin-7-one;

1-[4-[(1,3-benzodioxol-5-ylmethyl)amino]-6-chloro-2-quinazolinyl]-4-piperidinecarboxylic acid, monosodium salt;

Pharmaprojects No. 4516 (Glaxo Wellcome);
Pharmaprojects No. 5051 (Bayer);
Pharmaprojects No. 5064 (Kyowa Hakko; see WO 96/26940);
Pharmaprojects No. 5069 (Schering Plough);
GF-196960 (Glaxo Wellcome);
E-8010 and E-4010 (Eisai);
Bay-38-3045 & 38-9456 (Bayer);
Sch-51866;
pyrazolo[4,3d]pyrimidin-7-ones disclosed in EP-A-0463756;
pyrazolo[4,3-d]pyrimidin-7-ones disclosed in EP-A-0526004;
pyrazolo[4,3d]pyrimidin-7-ones disclosed in published international patent application WO 93/06104;
isomeric pyrazolo[3,4]pyrimidin-4-ones disclosed in published international patent application WO 93/07149;
quinazolin-4-ones disclosed in published international patent application WO 93/12095;
pyrido[3,2-d]pyrimdin-4-ones disclose in published international patent application WO 94/05661;
purin-6-ones disclosed in published international patent application WO 94/00453;
pyrazolo[4,3-d]pyrimidin-7-ones disclosed in published international patent application WO 98/49166;
pyrazolo[4,3-d]pyrimidin-7-ones disclosed in published international patent application WO 99/54333;
pyrazolo[4,3-d]pyrimidin-4-ones disclosed in EP-A-0995751;
pyrazolo[4,3-d]pyrimidin-7-ones disclosed in published international patent application WO 00/24745;
pyrazolo[4,3-d]pyrimidin-4-ones disclosed in EP-A-0995750;
the compounds disclosed in published international application WO 95/19978;
the compounds disclosed in published international application WO 99/24433 and
the compounds disclosed in published international application WO 93/07124.

It is to be understood that the contents of the above published patent applications, and in particular the general formulas and exemplified compounds therein, are incorporated in this specification in their entirety by reference thereto. It is further to be understood that the foregoing listing of PDE-5 inhibitors is intended to only be exemplary, and that other PDE-5 inhibitors, whether heretofore known or hereafter developed, may similarly be used in the practice of this invention.

The suitability of any particular PDE-5 inhibitor can be readily determined by evaluation of its potency and selectivity using literature methods followed by evaluation of its toxicity, absorption, metabolism, pharmacokinetics, etc. in accordance with standard pharmaceutical practice.

Preferably, the PDE-5 inhibitors have an $IC_{50}$ at less than 100 nanomolar, more preferably, at less than 50 nanomolar, more preferably still at less than 10 nanomolar.

Preferably, the PDE-5 inhibitors used according to the present invention are selective for the PDE-5 enzyme. More preferably, they are selective over PDE-3, more preferably still they are selective over PDE-3, PDE-4 and PDE-6. Preferably, the PDE-5 inhibitors of the invention have a selectivity ratio greater than 100, more preferably greater than 300, over PDE-3 and, more preferably, over PDE-3 and PDE-4. Selectivity ratios may be determined by the skilled person by means of any number of assays and tests known in the art.

Separate and Sequential Administration of Compounds for Treatment of Sexual Dysfunction.

In one embodiment, the invention includes separate and sequential administration of a PDE-5 inhibitor, such as sildenafil, and a melanocortin 3 and/or 4 receptor agonist, such as PT-141. By use of sequential administration, such as administration of an oral form of a PDE-5 inhibitor, followed by administration of an intranasal form of a melanocortin agonist, preferably wherein the administration of the intranasal form of a melanocortin agonist is a determined time interval subsequent to oral administration of a PDE-5 inhibitor, optimal therapeutic results may be obtained with minimal adverse side effects.

The present invention thus provides methods of treating sexual dysfunction, the methods comprising the steps of administering to the patient having or at risk of having sexual dysfunction a low dose, which need not be an independently therapeutically effective amount of a PDE-5 inhibitor, followed by a low dose, which need not independently be a therapeutically effective amount of a melanocortin agonist. Preferably, the PDE-5 inhibitor is administered within one hour, preferably within less than one-half hour, prior to administration of the melanocortin agonist.

In a preferred embodiment, a PDE-5 inhibitor, such as sildenafil, is administered prior to administration of PT-141, preferably between about 5 minutes and 45 minutes prior to administration of PT-141, more preferably between about 10 and 30 minutes prior, and more preferably still, between about 15 and 20 minutes prior to administration of PT-141. The PDE-5 inhibitor, such as sildenafil, is administered as an oral dose, preferably in a tablet formulation. The PT-141 dose is administered as an IN spray. It is known that systemic absorption is generally more rapid with intranasal administration than with oral administration; for example, with sildenafil, the time to optimal response is about one hour, though pharmacological responses are observed as early as 30 minutes following administration. However, IN PT-141 is rapidly absorbed in humans, reaching peak plasma levels at 30 minutes ($T_{max}$) with a half-life ($T_{1/2}$) of approximately 2 hours. Subcutaneous PT-141 has a $T_{max}$ of approximately 60 minutes and also has a $T_{1/2}$ of approximately 2 hours.

Synergistic Effect.

The dose of each of the PDE-5 inhibitor and PT-141 given as multiple agent therapy may be such as would be, for a particular patient, less than a therapeutic dose of either agent administered as monotherapy. For example, with a patient with erectile dysfunction refractory to PDE-5 inhibitor monotherapy, responsive only to a dose of 100 mg or more of sildenafil, it is possible to administer a lower dose of sildenafil, such as 25 mg or 50 mg, with administration, either before, concurrently or after a determined time, of a low dose of PT-141. The dose of PT-141 may be such that a given patient is not therapeutically responsive to such dose, such as an IN dose of 7.5 mg in a patient responsive only to higher doses, such as 15 or 20 mg of PT-141. In most patients, the oral dose of sildenafil is between about 25 and 50 mg, preferably about 25 mg, and the IN dose of PT-141 is between about 2.5 mg and 12.5 mg, preferably about 7.5 mg. However, as described hereafter higher doses may be employed in certain patient populations, such as patients who are marginally responsive to a PDE-5 inhibitor.

In general, in the practice of the invention, PT-141 is administered at a time after administration of the PDE-5 inhibitor at a time determined by, among other factors, the $T_{max}$ and half-life of the PDE-5 inhibitor. Thus, sildenafil has a median $T_{max}$ of 60 minutes, ranging from 30 to 120 minutes, and a half-life of about 4 hours. Thus, as described above, with IN PT-141, which has a $T_{max}$ of about 30 minutes, maximal therapeutic benefit of both agents theoretically results if PT-141 is administered about 30 minutes after sildenafil, and will be within the therapeutic window defined by the half-life of sildenafil if PT-141 is administered between about 5 minutes and several hours after sildenafil. Vardenafil has a similar $T_{max}$ and half-life as sildenafil, and thus may be similarly administered. However, tadalafil has a longer $T_{max}$, with a median reported $T_{max}$ of 2 hours, ranging from 30 minutes to 6 hours. The mean terminal half-life of tadalafil is significantly longer, about 17.5 hours. Additionally, with once-daily dosing of tadalafil, steady-state plasma concentrations are attained within 5 days, with exposure approximately 1.6-fold greater than after a single dose. While tadalafil is indicated for administration prior to anticipated sexual activity, given the half-life and steady-state plasma concentrations it may be taken on a once-daily basis. Thus PT-141 may be administered a significant period of time after tadalafil, such as preferably between about one and one-half hours after oral administration of tadalafil up to about 16 hours after oral administration of tadalafil. For patients taking tadalafil on a once-daily basis, PT-141 may be administered without regard to the time of dosing with tadalafil. Thus, for example, in a patient who is not therapeutically responsive to a low dose of tadalafil, such as 5 mg or 10 mg, or who is only marginally responsive to such dose, an oral dose of tadalafil could be taken between about one and one-half hours and about 16 hours prior to an IN dose of PT-141.

It has surprisingly and unexpectedly been found that multiple agent therapy, with either sequential or concurrent administration of the agents, will produce the desired pharmacological response, such as an erection sufficient for sexual intercourse, at a dose level of each agent given as multiple agent therapy that is less than a dose of either agent administered as monotherapy that produces the desired pharmacological response. Thus, multiple agent therapy, with sequential administration of the agents, produces a synergistic effect. It has further been surprisingly and unexpectedly found that multiple agent therapy, with sequential administration of the agents, will produce the desired pharmacological response where each agent is at a dose level such as to produce no or minimal adverse side effects. It has further been surprisingly and unexpectedly found that multiple agent therapy, with sequential administration of the agents, will produce a desired pharmacological response equivalent to the response obtainable only with a higher dose, generally a much higher dose, of single agent therapy (e.g., 100 mg of sildenafil administered alone as compared to 25 mg of sildenafil administered as multiple agent therapy with 7.5 mg of PT-141), without the adverse side effects associated with higher dose single agent therapy.

Study results, described in more detail hereafter in the examples, show statistically meaningful measures of the effectiveness of low dose multiple agent therapy compared to higher doses of single agent therapy. For example, comparisons of various erectile measurements were made in male subjects diagnosed with erectile dysfunction, which subjects received differing doses of sildenafil alone, or sildenafil followed by PT-141, as well as comparisons against normal human volunteers receiving PT-141 alone. Among the parameters measured over a 6.5 hour time course was the total time of penile base rigidity equal to or greater than 60%, where the subjects did not receive any visual or other sexual stimulation. A statistically significantly higher duration of base rigidity ($\geq 60\%$) was observed with sildenafil and IN PT-141 multiple agent therapy compared to sildenafil and IN placebo spray, or compared to placebo and IN PT-141. For example, the p values were less than 0.05 for comparisons of the results obtained with 50 mg of sildenafil and 10 mg of IN PT-141 to each of 50 mg of sildenafil alone, 100 mg of sildenafil alone, 7 mg of IN PT-141 alone (in normal human volunteers) and 10 mg of IN PT-141 alone (also in normal human voltuneers). Similar results were obtained with multiple agent therapy of 100 mg of sildenafil and 10 mg of IN PT-141. In other analyses of the data, p values as low as 0.0002 for base rigidity were obtained in comparisons of sildenafil and IN PT-141 to sildenafil and IN placebo spray.

That the effect was synergistic, and not merely additive, is seen by comparisons of mean durations of base rigidity, tip rigidity, or other measures of erectile function. For example, in measures of base rigidity $\geq 60\%$ with multiple agent therapy of 50 mg sildenafil and 10 mg IN PT-141 the mean duration in erectile dysfunction patients was 203 minutes. This is compared to a mean duration for 50 mg of sildenafil alone of 24.5 minutes in erectile dysfunction patients, and for 10 mg of IN PT-141 alone in normal human voltuneers, of 69 minutes. Thus the total time for each of 50 mg of sildenafil alone and 10 mg of IN PT-141 alone added together is only 93.5 minutes, less than half the mean time for multiple agent therapy. This result is particularly striking because the multiple agent therapy trials were conducted on men diagnosed with erectile dysfunction, while the studies in which only IN PT-141 was administered were conducted on normal healthy volunteers. Based on other trials, normal human volunteers have a substantially greater response to PT-141 by parameters such as duration than do patients with erectile dysfunction.

Advantageous Therapeutic Results.

It is known that PDE-5 inhibitors produce side effects or observed adverse events, most generally in a dose dependent fashion. That is, the incidence and/or severity of side effects is more pronounced as the dose level increases. For example, with sildenafil, the frequency of specific side effects are dose dependent, with commonly reported side effects including headache, flushing, upset stomach, stuffy nose, urinary tract infection, visual changes such as mild and temporary changes in blue/green colors or increased sensitivity to light, and diarrhea. Similarly, the frequency of PT-141 observed side effects are generally dose dependent, with an increased incidence of flushing, nausea, noxious aftertaste, post-nasal drip, headache, rhinorrhea, and vomiting at higher doses.

By either sequential or concurrent administration of low doses of two agents, one a PDE-5 inhibitor and one a melanocortin receptor agonist, it has been found that a therapeutic effect equal to or greater than that achieved with a single high dose of either agent given as monotherapy can be obtained, without the side effects incident to high dose administration of either agent as monotherapy. The effect is thus at least in part synergistic. Because of the intended therapeutic use, it is of substantial importance that side effects, such as nausea, be minimized. The invention and method provided herein permit inducing a therapeutic effect, particularly in patients for whom a low to moderate single agent dose is not effective, with minimal adverse side effects.

In general, adverse side effects are observed with greater frequency at doses of sildenafil of 50 mg or greater, and particularly at doses of 75 mg or 100 mg or greater. A substantial number of patients cannot tolerate doses of sildenafil of 100 mg or greater. However, for many of these patients a lesser dose, such as 25 or 50 mg of sildenafil, is sub-therapeutic, that is, does not initiate the desired pharmacological response in a patient, such as an erection of sufficient rigidity and duration for sexual intercourse. Similarly, adverse side effects are observed with greater frequency at doses of IN PT-141 of over 10 mg, such as doses of 20 mg of IN PT-141. Again, for many of these patients a lesser dose, such as 7.5 mg or 10 mg of IN PT-141, is sub-therapeutic, that is, does not initiate the desired pharmacological response in a patient, such as an erection of sufficient rigidity and duration for sexual intercourse. It has surprisingly and unexpectedly been found that multiple agent therapy, wherein each agent is independently a sub-therapeutic dose, with either sequential or concurrent administration of the agents, will produce the desired pharmacological response, such as an erection sufficient for sexual intercourse, without producing the frequency or severity of adverse side effects observed at a sufficiently high dose of either agent administered as monotherapy that produces a comparable pharmacological response. By way of example, sequential administration of 25 mg or 50 mg of sildenafil followed by 7.5 mg or 10 mg of IN PT-141 will produce a desired pharmacological response in a patient comparable to monotherapy with either 100 mg of sildenafil or 20 mg of IN PT-141, but without the frequency or severity of side effects or adverse events generally observed with monotherapy with either 100 mg of sildenafil or 20 mg of IN PT-141.

It has further surprisingly and unexpectedly been found that multiple agent therapy, wherein each agent is independently a sub-therapeutic dose, with either sequential or concurrent administration of the agents, will produce the desired pharmacological response, such as an erection sufficient for sexual intercourse, for a longer duration, such as measured in minutes, than with a sufficiently high dose of either agent administered as monotherapy that produces an erection sufficient for sexual intercourse.

It has further surprisingly and unexpectedly been found that multiple agent therapy, such as wherein each agent is independently a sub-therapeutic dose, with either sequential or concurrent administration of the agents, will produce the desired pharmacological response, such as an erection sufficient for sexual intercourse, with higher reliability than does a higher dose of either agent administered as monotherapy that in some instances produces the desired pharmacological response. It has been observed that a significant percentage of erectile dysfunction patients have a low reliability of response to therapy, particularly with a PDE-5 inhibitor such as sildenafil. Thus a patient may be responsive to a dose of between about 50 mg and 100 mg of sildenafil, but is responsive much less than 100% of the time, such as is responsive about 25% to about 50% of the time. Such patients are called "marginally responsive" herein. By use of multiple agent therapy, even wherein each agent is independently a sub-therapeutic dose, the rate of responsiveness is increased, such that the patient is responsive about 50% to about 100% of the time.

It has further surprisingly and unexpectedly been found that multiple agent therapy, including but not limited to wherein each agent is independently a sub-therapeutic dose, with either sequential or concurrent administration of the agents, will produce the desired pharmacological response, such as an erection sufficient for sexual intercourse, in patients with nerve damage, such as resulting from a prostatectomy or spinal cord injury, who are marginally responsive to a PDE-5 inhibitor such as sildenafil. Thus a patient may be marginally responsive to a dose of between about 50 mg and about 100 mg of sildenafil, but by use of multiple agent therapy, even wherein each agent is independently a sub-therapeutic dose, the responsiveness is increased, such that the desired pharmacological response, such as an erection sufficient for sexual intercourse, results.

By reference to FIG. 1, the synergistic effect of sequential administration of low doses of two agents, one a PDE-5 inhibitor and one a melanocortin receptor agonist, may be appreciated. As is seen in FIG. 1, a PDE-5 inhibitor attenuates the hydrolysis of cyclic guanosine monophosphate (cGMP, also called guanosine 3',5'-cyclic monophosphate), thereby increasing the persistence of cGMP, by inhibiting the activity of endogenous type V phosphodiesterase (PDE-5), it being understood that PDE-5 naturally regulates the degradation of cGMP to 5' guanosine monophosphate (5' GMP) in the corpus cavernosum. By contrast, PT-141 is believed to have at least one mechanism of action, relating to activation of melanocortin receptors, in the induction of penile erection by directly increasing cGMP production. In sum, it is believed that, at least in part, PT-141 results in increased production of nitric oxide (NO) synthesized from neuronal nitric oxide synthase (nNOS), with the NO activating soluble guanylate cyclase to catalyze the conversion of guanosine triphosphate (GTP, also called guanosine 5'-triphosphate) to cGMP. It may thus be seen that by manipulating two different pathways, the effect of a PDE-5 inhibitor, such as sildenafil, and a melanocortin receptor agonist, such as PT-141, on cGMP are synergistic. This further has implications with respect to the invention herein; in part, it may be seen that it is desirable to concomitantly inhibit PDE-5 and increase production of cGMP by means of different pathways, thereby resulting in optimal therapeutic benefit with minimal adverse effects.

The invention is further illustrated by the following non-limiting examples.

EXAMPLE 1

In a human clinical study, a group of nineteen male patients suffering from erectile dysfunction were evaluated in a placebo-controlled, randomized, double-blind, three-way crossover trial. Each clinical study participant received, in randomized fashion: (1) 25 mg of sildenafil followed 5 minutes later by IN administration of 7.5 mg of PT-141 (Test One), (2) 25 mg of sildenafil without PT-141 (Test Two), and (3) only a placebo (Test Three). Subjects were selected who had a diagnosis of erectile dysfunction and were responsive to either sildenafil or vardenafil, typically between 50 and 100 mg of sildenafil. Placebo treatment consisted of a placebo tablet and placebo spray; in Test Two and Test Three, placebos were appropriately administered, with study participants blindfolded while receiving either an oral form of sildenafil or placebo tablet to maintain the blind.

During the study, a RigiScan® device, as hereafter described, was attached 30 minutes pre-dose (T-30), where subjects were dosed at T0, with a first 30 minute visual sexual stimulation (VSS) session, utilizing subject-selected sexually graphic videos, occurring from 50 to 80 minutes post-dose (T50 to T80), and a second 30 minute VSS session occurring from 110 to 140 minutes post-dose (T110 to T140), with the RigiScan®) device continuing to monitor the subject until six (6) hours post-dose (a total of 6.5 hours). All times were relative to administration of the IN dose of PT-141 or IN placebo. The RigiScan® device was a RigiScan® Plus Rigidity Assessment System device used to objectively quantitate penile rigidity and tumescence (Timm Medical Technologies, Eden Prairie, Minn., USA). The RigiScan® Plus is a portable, self-contained plethysmography device worn in a holster-like case on the thigh. The device measures radial rigidity and tumescence. Two strain gauge loops were placed at both the tip and base of the penis. The loops were firmly squeezed around the base of the penis and at the tip, immediately behind the corona of the glans. The loops squeeze the penile shaft with a constant force; the softer penile shaft is more easily compressed, resulting in a greater circumferential difference. RigiScan® Plus measures this displacement, and expressed the rigidity of the shaft as a percent: when the penis is fully erect, and the displacement zero, the rigidity equals 100%; when the penis fails to achieve any rigidity and the displacement is maximal, the rigidity is recorded at 0%. The device internally recorded penile response from the loops, with the results downloaded to a computer for analysis by the system's specifically designed software. The RigiScan® Plus Rigidity Assessment System assessed radial rigidity, base and tip, every 15 seconds, once the subject's baseline tumescence was exceeded by 1 cm. Base and tip tumescence were also automatically calculated by the RigiScan® device.

Rigiscan® data was collected on all subjects. Specific analyses included the total time of 60% or greater penis base rigidity for all events that began at any time point within thirty minutes post dosing and up to 180 minutes post dosing, and independently included all results with 60% or greater penis base rigidity for the full 6.5 hour period. Data were analyzed by analysis of variance (ANOVA) methods, utilizing a mixed model including sequence and period effect in the model. The following tables include the mean results for each group, and p values for each listed comparison, wherein a p value of 0.05 or less is presumptively statistically significant.

As is shown in Table 1 below, the overall ANOVA p value was 0.0167, indicating that the distribution between Test One, Two and Three during the 6.5 hour session was non-random. The differences between both Test One versus Test Two (sildenafil followed by PT-141 versus sildenafil alone) and Test One versus Test Three (sildenafil followed by PT-141 versus placebo) were statistically significant, while over the 6.5 hour observation period the difference in the time >60% base rigidity after sildenafil treatment alone was not statistically significant as compared to placebo treatment (Test Two versus Test Three).

TABLE 1

Rigiscan Base Rigidity ≧ 60% (minutes) (6.5 hour observation period)

|  | Mean (minutes) | ANOVA p | Test 1 vs. 2 p | Test 1 vs. 3 p | Test 2 vs. 3 p |
| --- | --- | --- | --- | --- | --- |
| Test One | 108.21 | 0.0016 | 0.0167 | 0.0004 | 0.1650 |
| Test Two | 65.42 | | | | |
| Test Three | 41.99 | | | | |

Figure 2:
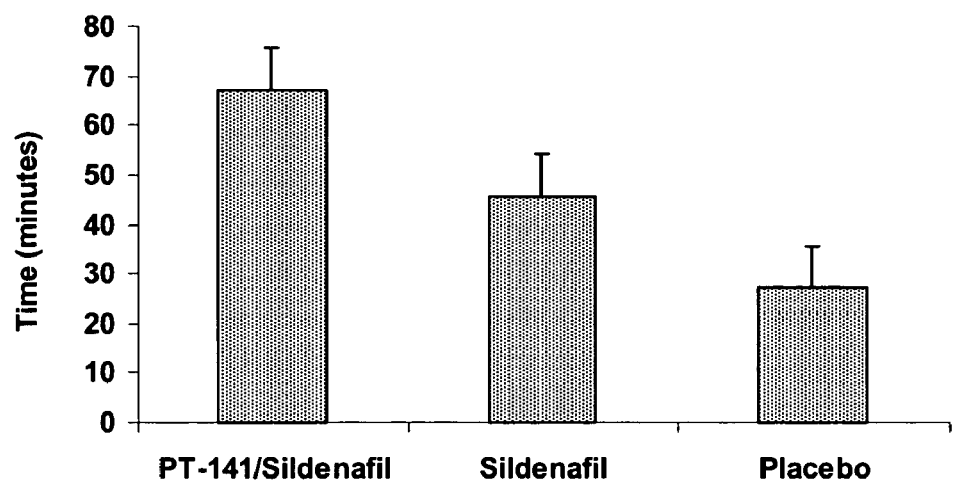
FIG. 2 is a chart illustrating the mean duration (minutes) of base rigidity, with standard error shown in error bars, at $\geq 60\%$ during a 2.5-hour monitoring session (30 minutes after dose to 3 hours after dose), comparing multiple agent therapy of 25 mg of sildenafil co-administered with 7.5 mg IN PT-141 to 25 mg of sildenafil alone and to placebo.

The data were similarly analyzed over a 2.5 hour period, a period from approximately 30 minutes post-PT-141 administration to the conclusion of the second VSS session. These data are shown in Table 2 below and in FIG. 2.

TABLE 2

Rigiscan Base Rigidity ≧ 60% (minutes) (2.5 hour observation period)

|  | Mean (minutes) | ANOVA p | Test 1 vs. 2 p | Test 1 vs. 3 p | Test 2 vs. 3 p |
| --- | --- | --- | --- | --- | --- |
| Test One | 67.37 | 0.0002 | 0.0170 | <0.0001 | 0.0313 |
| Test Two | 45.99 | | | | |
| Test Three | 27.43 | | | | |

Here too, the overall ANOVA p value was significant, 0.0002, indicating that the distribution between Test One, Two and Three was non-random. The differences between both Test One versus Test Two (sildenafil followed by PT-141 versus sildenafil alone) and Test One versus Test Three (sildenafil followed by PT-141 versus placebo) were highly statistically significant, and Test Two versus Test Three (sildenafil alone versus placebo) was also significant (0.0313).

A blinded patient-reported assessment of the effectiveness of therapy in terms of quality of erection for each of Test One, Two and Three was also conducted, with assessments completed following the completion of each VSS session, utilizing a ranking scale of 1 (worst) to 10 (best). The mean of each of the two assessments for each test group were calculated, with a mean raw score of 7.37 for Test One (sildenafil followed by PT-141), 6.21 for Test Two (sildenafil alone) and 5.13 (placebo). In an analysis based on the higher of the two assessments for each patient, the mean raw score for Test One (sildenafil followed by PT-141) was 8.16, for Test Two (sildenafil alone) was 6.79 and for Test Three (placebo) was 5.74. Statistical analysis, utilizing a two-tailed, paired student's t test, determined that the p value for Test One versus Test Two (sildenafil followed by PT-141 versus sildenafil alone) was 0.0212, and Test One versus Test Three (sildenafil followed by PT-141 versus placebo) was 0.0002, both statistically significant, with Test Two versus Test Three (sildenafil alone versus placebo) being 0.0786, and not considered statistically significant.

Of additional significance, in analyzing the data for the higher of the two assessments, the Test One (sildenafil followed by PT-141) group contained 5 of 19 patients scoring a "10", and 4 of 19 patients scoring a "9". By contrast, the Test Two (sildenafil alone) group contained only one "10" out of 19 patients, with 4 of 19 patients scoring a "9". The Test Three (placebo) group similarly contained only one "10" out of 19 patients, and 2 of 19 patients scoring a "9". A number of patients taking sildenafil prior to the study (a study inclusion criteria) further reported that the quality of erections in the Test One group was superior to that experienced by those patients taking prescription sildenafil (Viagra®).

No serious or unexepcted drug-associated adverse effects were reported or noted in any patients for Test One, Test Two or Test Three. In both the Test One and Test Two groups, side effects were consistent with those observed for comparable low doses of either sildenafil or PT-141 in other studies. Importantly, multiple agent therapy of a low dose of each of sildenafil and PT-141 appeared to result in a thereapeutic benefit equivalent to a pharmacologically active higher dose of either agent as monotherapy, without the attendant adverse events associated with higher dose monotherapy.

EXAMPLE 2

In a second human clinical study, a group of thirty-two male patients suffering from erectile dysfunction were evaluated in a placebo-controlled, randomized, double-blind, escalating-dose drug interaction study involving co-administered doses of IN PT-141 and sildenafil. Subjects within each dose group received a single dose of sildenafil co-administered with a single dose of IN PT-141 or placebo spray at a 3:1 ratio; in each dose group of 8 subjects, 6 subjects received sildenafil and PT-141 and 2 subjects received sildenafil and placebo spray. Sildenafil doses were 50 mg and 100 mg. PT-141 doses were 7.5 mg and 10 mg. Dose escalation to the next higher dose group did not occur until all subjects within a dose group had received study medication and had satisfactorily tolerated the current dose level. Study measurements included vital signs, ECG evaluations, spontaneous adverse event (AE) reports, and assessment of penile rigidity by RigiScan® monitoring for a total period of six and one-half hours. No form of erotic or sexual stimulation was used in this study. Subjects were screened and enrolled based upon medical and sexual history, evidence of a diagnosis of erectile dysfunction of at least 6 months duration, clinical laboratory results, electrocardiogram, and physical examination.

The subjects were randomized to one of the treatment paths in Table 3. Treatment paths 1–4 were consecutively conducted, with safety assessments following each treatment path.

TABLE 3

| Treatment Path | N | Treatment |
| --- | --- | --- |
| 1 | 8 | 50 mg sildenafil + 7.5 mg IN PT-141 (n = 6) or 50 mg sildenafil + Placebo Spray (n = 2) |
| 2 | 8 | 50 mg sildenafil + 10 mg IN PT-141 (n = 6) or 50 mg sildenafil + Placebo Spray (n = 2) |
| 3 | 8 | 100 mg sildenafil + 7.5 mg IN PT-141 (n = 6) or 100 mg sildenafil + or Placebo Spray (n = 2) |
| 4 | 8 | 100 mg sildenafil + 10 mg IN PT-141 (n = 6) or 100 mg sildenafil + Placebo Spray (n = 2) |

IN PT-141 or placebo spray was administered to the nostril with greater patency five minutes after the sildenafil tablet was swallowed. RigiScan® monitoring occurred from 30 minutes pre-dose until 6 hours post-dose.

There was clear evidence of increased erectile response following sildenafil and IN PT-141 co-administration compared to sildenafil and placebo spray based on the RigiScan® plethysmography monitoring. Co-administration of sildenafil and IN PT-141 resulted in statistically significantly greater duration of base and tip rigidity ≧60%, base rigidity ≧80%, and base and tip defined "Rigidity Activity Units" (RAU) and "Tumescence Activity Units" (TAU) compared to sildenafil and placebo (p<0.05), based on a two-way analysis of variance.

Figure 3:
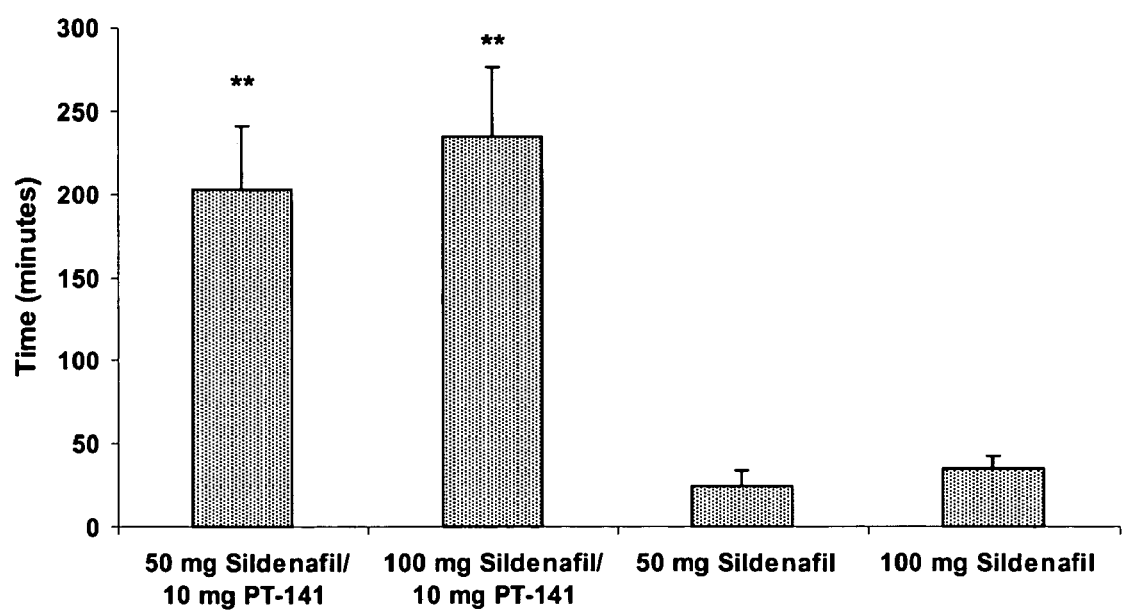
FIG. 3 is a chart illustrating the mean duration (minutes) of rigidity at $\geq 60\%$ during a 6.5-hour monitoring session, comparing multiple agent therapy with 50 mg or 100 mg of sildenafil co-administered with 10 mg IN PT-141 compared to either 50 mg or 100 mg of sildenafil alone (where "**" is $p<0.01$)

Data on duration of base rigidity ≧60% is shown in Table 4 and FIG. 3. Based upon analysis of variance (two-way ANOVA), a statistically significantly higher duration of base and tip rigidity ≧60% was observed with sildenafil and IN PT-141 co-administration compared to sildenafil and IN placebo spray (p=0.0003 for base, p=0.0221 for tip).

TABLE 4

Summary Statistics for Duration (in Minutes) of RigiScane® Base and Tip Rigidity ≧ 60% During RigiScan Monitoring Following Study Medication by Treatment

| | Treatment | | | | | |
| --- | --- | --- | --- | --- | --- | --- |
| | 50 mg Sildenafil and 7.5 mg PT-141 | 50 mg Sildenafil and 10 mg PT-141 | 50 mg Sildenafil and Placebo Spray | 100 mg Sildenafil and 7.5 mg PT-141 | 100 mg Sildenafil and 10 mg PT-141 | 100 mg Sildenafil and Placebo Spray |
| | | | N | | | |
| | 6 | 6 | 4 | 6 | 6 | 3 |
| | Duration of Base Rigidity ≧ 60% | | | | | |
| Mean | 115.25 | 203.00 | 24.50 | 67.92 | 234.83 | 89.17 |
| SD | 71.48 | 92.66 | 18.63 | 79.30 | 102.63 | 92.80 |
| Median | 132.75 | 254.25 | 26.50 | 54.75 | 268.50 | 43.00 |
| Minimum | 2.00 | 59.00 | 0.00 | 4.50 | 38.00 | 28.50 |
| Maximum | 185.50 | 273.00 | 45.00 | 220.50 | 314.50 | 196.00 |

TABLE 4-continued

Summary Statistics for Duration (in Minutes) of RigiScane ® Base and Tip Rigidity ≧ 60% During RigiScan Monitoring Following Study Medication by Treatment

| | Treatment | | | | | |
|---|---|---|---|---|---|---|
| | 50 mg Sildenafil and 7.5 mg PT-141 | 50 mg Sildenafil and 10 mg PT-141 | 50 mg Sildenafil and Placebo Spray | 100 mg Sildenafil and 7.5 mg PT-141 | 100 mg Sildenafil and 10 mg PT-141 | 100 mg Sildenafil and Placebo Spray |
| | | | N | | | |
| | 6 | 6 | 4 | 6 | 6 | 3 |
| | Duration of Tip Rigidity ≧ 60% | | | | | |
| Mean | 82.25 | 168.08 | 15.00 | 59.92 | 139.17 | 95.17 |
| SD | 60.68 | 91.24 | 13.61 | 70.56 | 120.89 | 90.97 |
| Median | 99.75 | 172.25 | 15.25 | 38.50 | 135.50 | 48.50 |
| Minimum | 1.00 | 57.00 | 0.00 | 2.50 | 7.00 | 37.00 |
| Maximum | 151.00 | 277.50 | 29.50 | 193.50 | 292.50 | 200.00 |

Data on duration of base rigidity ≧ 80% is shown in Table 5. Based upon analysis of variance, a statistically significantly higher duration of rigidity ≧ 80% was observed for the base (p=0.0087) for sildenafil and IN PT-141 co-administration vs. sildenafil and IN placebo spray.

As summarized in Tables 6 and 7, co-administration of sildenafil and IN PT-141 resulted in significantly greater RAU and TAU for both the base and tip compared to sildenafil and IN placebo spray. Based upon analysis of variance, the effect of co-administration of sildenafil and

TABLE 5

Summary Statistics for Duration (in Minutes) of RigiScan ® Base and Tip Rigidity ≧ 80% During RigiScan Monitoring Following Study Medication by Treatment

| | Treatment | | | | | |
|---|---|---|---|---|---|---|
| | 50 mg Sildenafil and 7.5 mg PT-141 | 50 mg Sildenafil and 10 mg PT-141 | 50 mg Sildenafil and Placebo Spray | 100 mg Sildenafil and 7.5 mg PT-141 | 100 mg Sildenafil and 10 mg PT-141 | 100 mg Sildenafil and Placebo Spray |
| | | | N | | | |
| | 6 | 6 | 4 | 6 | 6 | 3 |
| | Duration of Base Rigidity ≧ 80% | | | | | |
| Mean | 41.08 | 109.42 | 12.25 | 47.75 | 131.58 | 55.50 |
| SD | 30.57 | 85.62 | 9.26 | 73.88 | 72.35 | 69.78 |
| Median | 42.50 | 83.50 | 14.00 | 20.50 | 143.00 | 32.00 |
| Minimum | 0.50 | 22.00 | 0.00 | 0.00 | 4.00 | 0.50 |
| Maximum | 83.00 | 240.00 | 21.00 | 195.00 | 220.50 | 134.00 |
| | Duration of Tip Rigidity ≧ 80% | | | | | |
| Mean | 33.58 | 121.08 | 8.50 | 46.25 | 63.83 | 73.67 |
| SD | 43.21 | 76.00 | 10.87 | 57.01 | 95.92 | 75.96 |
| Median | 9.25 | 95.50 | 5.25 | 34.75 | 31.25 | 41.00 |
| Minimum | 0.00 | 54.00 | 0.00 | 0.50 | 2.00 | 19.50 |
| Maximum | 94.00 | 237.50 | 23.50 | 155.00 | 256.50 | 160.50 |

PT-141 was significantly greater than that of sildenafil and IN placebo spray (RAU: p=0.0004 for base, p=0.0160 for tip; TAU: p=0.0006 for base, p=0.0179 for tip).

No subjects discontinued study participation due to adverse events, and no serious adverse events were reported during the study.

TABLE 6

Summary Statistics for Rigidity Activity Units (RAU) for Base and Tip During RigiScan ® Monitoring Following Study Medication by Treatment

| | Treatment | | | | | |
|---|---|---|---|---|---|---|
| | 50 mg Sildenafil and 7.5 mg PT-141 | 50 mg Sildenafil and 10 mg PT-141 | 50 mg Sildenafil and Placebo Spray | 100 mg Sildenafil and 7.5 mg PT-141 | 100 mg Sildenafil and 10 mg PT-141 | 100 mg Sildenafil and Placebo Spray |
| N | 6 | 6 | 4 | 6 | 6 | 3 |
| Base Rigidity Activity Units (RAU) | | | | | | |
| Mean | 101.00 | 165.50 | 27.25 | 61.00 | 192.50 | 57.00 |
| SD | 61.91 | 84.92 | 19.35 | 73.32 | 80.38 | 27.22 |
| Median | 109.00 | 203.50 | 33.50 | 37.50 | 217.50 | 53.00 |
| Minimum | 2.00 | 26.00 | 0.00 | 6.00 | 38.00 | 32.00 |
| Maximum | 168.00 | 242.00 | 42.00 | 201.00 | 251.00 | 86.00 |
| Tip Rigidity Activity Units (RAU) | | | | | | |
| Mean | 78.50 | 138.67 | 21.50 | 54.83 | 122.67 | 56.67 |
| SD | 54.36 | 78.82 | 14.43 | 66.78 | 95.83 | 31.94 |
| Median | 100.00 | 149.50 | 27.50 | 30.50 | 114.50 | 44.00 |
| Minimum | 2.00 | 27.00 | 0.00 | 3.00 | 27.00 | 33.00 |
| Maximum | 137.00 | 235.00 | 31.00 | 179.00 | 259.00 | 93.00 |

TABLE 7

Summary Statistics for Tumescence Activity Units (TAU) for Base and Tip During RigiScan ® Monitoring Following Study Medication by Treatment

| | Treatment | | | | | |
|---|---|---|---|---|---|---|
| | 50 mg Sildenafil and 7.5 mg PT-141 | 50 mg Sildenafil and 10 mg PT-141 | 50 mg Sildenafil and Placebo Spray | 100 mg Sildenafil and 7.5 mg PT-141 | 100 mg Sildenafil and 10 mg PT-141 | 100 mg Sildenafil and Placebo Spray |
| N | 6 | 6 | 4 | 6 | 6 | 3 |
| Base Rigidity Activity Units (TAU) | | | | | | |
| Mean | 62.17 | 100.17 | 19.00 | 30.00 | 99.67 | 34.69 |
| SD | 52.89 | 46.49 | 17.63 | 29.41 | 34.34 | 14.01 |
| Median | 52.50 | 108.50 | 18.00 | 24.50 | 100.50 | 39.00 |
| Minimum | 3.00 | 26.00 | 0.00 | 1.00 | 43.00 | 19.00 |
| Maximum | 151.00 | 146.00 | 40.00 | 82.00 | 150.00 | 46.00 |
| Tip Rigidity Activity Units (TAU) | | | | | | |
| Mean | 53.00 | 95.33 | 16.25 | 26.50 | 59.83 | 46.67 |
| SD | 50.95 | 40.88 | 14.45 | 29.94 | 38.83 | 31.50 |
| Median | 50.50 | 100.50 | 15.00 | 15.50 | 58.50 | 47.00 |
| Minimum | 2.00 | 20.00 | 0.00 | 1.00 | 21.00 | 15.00 |
| Maximum | 145.00 | 144.00 | 35.00 | 81.00 | 101.00 | 78.00 |

The majority of adverse events were mild in intensity. There were no particular adverse events that appeared to be accentuated or worsened, either in frequency or severity, by co-administration of sildenafil and IN PT-141. No instances of painful, prolonged erections or priapism were reported.

EXAMPLE 3

Figure 4:
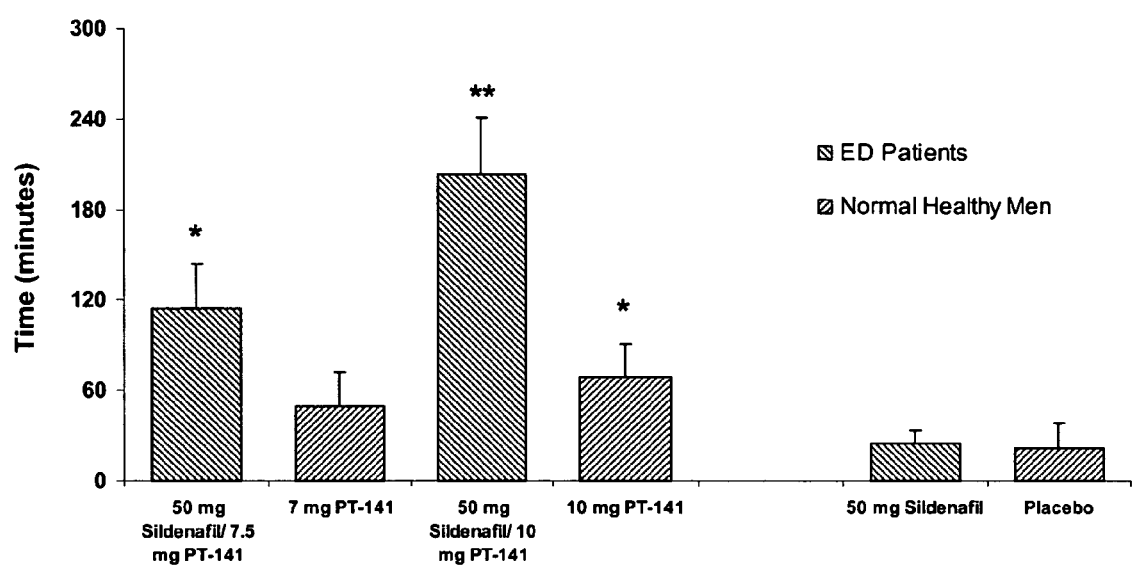
FIG. 4 is a chart illustrating the mean duration (minutes) of base rigidity at $\geq 60\%$ during a 6.5-hour monitoring session, comparing multiple agent therapy in erectile dysfunction subjects with 50 mg of sildenafil co-administered with 7.5 mg of IN PT-141 or 50 mg of sildenafil co-administered with 10 mg of IN PT-141 compared to 50 mg of sildenafil alone, 7 mg of IN PT-141 alone (normal human volunteers), 10 mg of IN PT-141 alone (normal human volunteers) or placebo (where "*" is $p<0.05$ and "**" is $p<0.01$).

Data from studies conducted with normal human volunteers, but otherwise identical to the protocols for Example 2, was compared to the results obtained in Example 2. Thus the only difference was that normal human volunteers, who are more responsive to erectogenic drugs than persons diagnosed with erectile dysfunction were the study subjects. Normal human volunteers were administered 7 mg or 10 mg of IN PT-141, and were tested as in Example 2, employing RigiScan® monitoring for a total period of six and one half hours. For measures of duration of base rigidity ≧60%, the results obtained with either 50 mg sildenafil and 10 mg IN PT-141, or alternatively 100 mg sildenafil and 10 mg IN PT-141 (both erectile dysfunction patients), were statistically significantly greater (p<0.05) than the results obtained with any one of 50 mg sildenafil, 100 mg sildenafil, 7 mg IN PT-141 or 10 mg IN PT-141. Results are shown graphically on FIG. 4. Similarly measures of duration of base rigidity ≧80% were statistically significantly greater for multiple agent therapy with 50 mg sildenafil and 10 mg IN PT-141, or alternatively 100 mg sildenafil and 10 mg IN PT-141, for 50 mg sildenafil, 7 mg IN PT-141 or 10 mg IN PT-141.

A synergistic effect was also observed, wherein the values of duration of the added mean durations of both monotherapies independently was substantially less than the mean duration of multiple agent therapies, all at the same dose levels for each component. The mean values are shown on Table 8.

TABLE 8

| Duration of Base Rigidity ≧ 60% (minutes) | |
|---|---|
| 50 mg sildenafil (ED) | 24.5 |
| 7 mg IN PT-141 (NHV) | 49.4 |
| Subtotal | 73.9 |
| 50 mg sildenafil + 7.5 mg IN PT-141 (ED) | 115.2 |
| 50 mg sildenafil (ED) | 24.5 |
| 10 mg IN PT-141 (NHV) | 69.2 |
| Subtotal | 93.7 |
| 50 mg sildenafil + 10 mg IN PT-141 (ED) | 203.0 |
| 100 mg sildenafil (ED) | 89.3 |
| 10 mg IN PT-141 (NHV) | 69.2 |
| Subtotal | 158.5 |
| 100 mg sildenafil + 10 mg IN PT-141 (ED) | 234.8 |

In Table 8, "ED" refers to patients diagnosed with erectile dysfunction, with data extracted from Example 2. "NHV" refers to normal human volunteers.

Similarly, maximum values obtained in duration of parameters relating to erectile function were generally substantially greater for multiple agent therapy than the additive results obtained with the same dose of each independent agent as monotherapy. For example, with the measure of the duration of base rigidity ≧60%, the maximum value obtained for 50 mg sildenafil and 10 mg IN PT-141 was 273 minutes, while the maximum value for 50 mg sildenafil alone was 45 minutes, and the maximum value, but in normal human volunteers, for 10 mg of IN PT-141 alone was 134.5 minutes.

EXAMPLE 4

Female patients diagnosed with female sexual dysfunction are orally administered a dose of either 25 mg or 50 mg of sildenafil. Between about 5 minutes and one hour later, the patients are nasally administered a dose of between 5 mg and 10 mg of PT-141.

EXAMPLE 5

Male patients diagnosed with erectile dysfunction are orally administered tadalafil on a once-daily dose of between 5 mg and 10 mg. Between about 15 minutes and two hours prior to desired initiation of sexual activity, the patients are nasally administered a dose of between 5 mg and 10 mg of PT-141.

EXAMPLE 6

Male patients diagnosed with erectile dysfunction and marginally responsive to once-daily doses of 20 mg of tadalafil (responsive for less than about 50% of attempted sexual activity) are orally administered 20 mg of tadalafil on a once-daily schedule. Between about 15 minutes and two hours prior to desired initiation of sexual activity, the patients are nasally administered a dose of between 10 mg and 20 mg of PT-141.

EXAMPLE 7

Male patients diagnosed with erectile dysfunction and marginally responsive to doses of up to 100 mg of sildenafil (responsive for less than about 50% of attempted sexual activity) are orally administered between 50 and 100 mg of sildenafil between about one and two hours prior to desired initiation of sexual activity. Between about 5 minutes and one hour after ingesting the oral sidenafil, the patients are nasally administered a dose of between 10 mg and 20 mg of PT-141.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of treating sexual dysfunction in a patient, comprising:
   oral administration of a quantity of a type V phosphodiesterase (PDE-5) inhibitor; and
   non-oral administration of a quantity of Ac-Nle-cyclo(-Asp-His-D-Phe-Arg-Trp-Lys)-OH (PT-141),
   wherein the quantity of the PDE-5 inhibitor and the quantity of PT-141 are together sufficient to produce synergistic effect in the treatment of sexual dysfunction in the patient.

2. The method of claim 1, wherein the non-oral administration of PT-141 is intranasal.

3. The method of claim 1, wherein the quantity of PDE-5 inhibitor administered is not sufficient to initiate a desired pharmacological response in treating sexual dysfunction in the patient when administered as a monotherapy.

4. The method of claim 2, wherein the quantity of PT-141 administered is not sufficient to initiate a desired pharmacological response in treating sexual dysfunction in the patient when administered as a monotherapy.

5. The method of claim 1, wherein the patient is a male patient, the sexual dysfunction is erectile dysfunction, and a desired pharmacological response comprising the ability to attain an erection of sufficient rigidity for sexual intercourse, the ability to sustain an erection of sufficient rigidity for sexual intercourse or a combination thereof is obtained.

6. The method of claim 1 wherein the PDE-5 inhibitor is sildenafil, vardenafil or tadalafil.

7. The method of claim 6, wherein the PDE-5 inhibitor is sildenafil, the quantity of sildenafil administered is between about 25 mg and about 100 mg and the quantity of PT-141 administered is between about 2.5 mg and about 15 mg.

8. The method of claim 6, wherein the PDE-5 inhibitor is sildenafil, the quantity of sildenafil is about 25 mg and the quantity of PT-141 is about 7.5 mg.

9. The method of claim 6, wherein the PDE-5 inhibitor is sildenafil, the quantity of sildenafil administered is no more than about 25 mg and the quantity of PT-141 administered is no more than about 10 mg.

10. The method of claim 1, wherein the PDE-5 inhibitor is administered prior to administration of PT-141.

11. The method of claim 1, wherein the PDE-5 inhibitor is administered between about 5 and 45 minutes prior to administration of PT-141.

12. The method of claim 1, wherein the PDE-5 inhibitor is administered between about 10 and 30 minutes prior to administration of PT-141.

13. The method of claim 1, wherein PT-141 is administered about 30 minutes prior to the attainment of the average peak plasma concentration ($T_{max}$) of the PDE-5 inhibitor.

14. The method of claim 1, wherein PT-141 is administered no later than about 30 minutes prior to the end of the average half-life of the PDE-5 inhibitor.

15. The method of claim 1, wherein the PDE-5 inhibitor is administered so as to maintain a steady-state plasma concentration and PT-141 is administered thereafter while the PDE-5 inhibitor is at the steady-state plasma concentration.

16. The method of claim 15, wherein the PDE-5 inhibitor is tadalafil.

17. The method of claim 1, wherein:
the patient is a male patient,
the sexual dysfunction is erectile dysfunction,
the quantity of PDE-5 inhibitor administered is less than that required to treat erectile dysfunction using the PDE-5 inhibitor as a monotherapy,
the quantity of PT-141 administered is less than that required to treat erectile dysfunction using PT-141 as a monotherapy, and
the quality of erection score obtained is superior to that obtained from (i) administration of the PDE-5 inhibitor as a monotherapy in a therapeutically effective amount sufficient to treat erectile dysfunction in the patient, or (ii) administration of PT-141 as a monotherapy in a therapeutically effective amount sufficient to treat erectile dysfunction in the patient.

18. A method of treating erectile dysfunction in a patient, comprising:
oral administration of a PDE-5 inhibitor; and
intranasal administration of a quantity of PT-141 of less than about 12 mg,
wherein the PDE-5 inhibitor is administered prior to intranasal administration of PT-141,
and wherein the quantity of the PDE-5 inhibitor and the quantity of PT-141 are together effective to treat erectile dysfunction in the patient.

19. A method of decreasing side effects associated with therapeutic agents for treating sexual dysfunction in a patient, comprising:
oral administration of a quantity of PDE-5 inhibitor, wherein the quantity of PDE-5 inhibitor administered is not sufficient to initiate a desired pharmacological response treating sexual dysfunction in the patient when administered as a monotherapy; and
non-oral administration of a quantity of PT-141, wherein the quantity of PT-141 administered is not sufficient to initiate the desired pharmacological response in treating sexual dysfunction in the patient when administered as a monotherapy,
wherein the quantity of the PDE-5 inhibitor and the quantity of PT-141 are together effective to initiate the desired pharmacological response in treating sexual dysfunction in the patient,
thereby reducing side effects in the treatment of sexual dysfunction in the patient.

20. A method of treating sexual dysfunction in a patient marginally responsive to a PDE-5 inhibitor, comprising the steps of:
establishing a dose of a PDE-5 inhibitor at which the patient has marginal responsiveness with respect to treating sexual dysfunction with the PDE-5 inhibitor;
oral administration of the marginally responsive dose of the PDE-5 inhibitor; and
non-oral administration of a Quantity of PT-141, wherein the dose of the PDE-5 inhibitor
and the Quantity of PT-141 are effective to increase the responsiveness with
respect to treating sexual dysfunction in the patient.

21. The method of claim 20, wherein the step of establishing a dose of a PDE-5 inhibitor to which the patient is marginally responsive comprises:
establishing a dose of a PDE-5 inhibitor at which the patient is responsive about 25% to about 50% of the time.

22. The method of claim 20, wherein sexual dysfunction is erectile dysfunction.

* * * * *

UNITED STATES PATENT AND TRADEMARK OFFICE
CERTIFICATE OF CORRECTION

| | | |
|---|---|---|
| PATENT NO. | : 7,235,625 B2 | Page 1 of 1 |
| APPLICATION NO. | : 11/139730 | |
| DATED | : June 26, 2007 | |
| INVENTOR(S) | : Diamond et al. | |

It is certified that error appears in the above-identified patent and that said Letters Patent is hereby corrected as shown below:

Col. 30, Claim 19, line 17, please delete "response treating" and replace with -- response in treating --;

Col. 30, Claim 20, line 38, please delete "Quantity" and replace with -- quantity --.

Col. 30, Claim 20, line 40, please delete "Quantity" and replace with -- quantity --.

Signed and Sealed this

Twenty-seventh Day of November, 2007

JON W. DUDAS
*Director of the United States Patent and Trademark Office*